US008290192B2

(12) United States Patent
Wong et al.

(10) Patent No.: US 8,290,192 B2
(45) Date of Patent: Oct. 16, 2012

(54) GAMING HEADSET VIBRATOR

(75) Inventors: John Patrick Wong, Vancouver (CA); Jeff Crampton, Vancouver (CA)

(73) Assignee: Nokia Corporation, Espoo (FI)

(*) Notice: Subject to any disclaimer, the term of this patent is extended or adjusted under 35 U.S.C. 154(b) by 2297 days.

(21) Appl. No.: 11/050,140

(22) Filed: Feb. 3, 2005

(65) Prior Publication Data

US 2006/0171553 A1 Aug. 3, 2006

(51) Int. Cl.

| | |
|---|---|
| ***A61F 11/06*** | (2006.01) |
| ***H04R 1/10*** | (2006.01) |
| ***H04R 25/00*** | (2006.01) |
| ***A63F 9/24*** | (2006.01) |

(52) U.S. Cl. ............ 381/332; 381/72; 381/74; 381/370; 381/380; 463/35; 463/37; 463/30; 463/47

(58) Field of Classification Search .................. 381/332, 381/74, 370, 380, 150, 151, 72; 463/47, 463/30, 35, 37
See application file for complete search history.

(56) References Cited

U.S. PATENT DOCUMENTS

| | | | | |
|---|---|---|---|---|
| 6,369,312 | B1 * | 4/2002 | Komatsu | 84/723 |
| 7,324,655 | B2 * | 1/2008 | Sato | 381/370 |
| 2004/0185915 | A1 | 9/2004 | Ihara et al. | |

OTHER PUBLICATIONS

CNET Editor's Review of the RCA HP900m Jun. 11, 2004. Reviewed by Nathaniel Wilkins, edited by John P. Falcone.*

Game Warehouse, Audio FX Vibrationg Headset, Retrieved Feb. 3, 2005. Release date 53/2004 http://www.gameswarehouse.com.au/band2.asp?gameid=9780, pp. 1-2.*

CNET Editor's Review of the RCA HP 900 Jun. 11, 2004. Reviewed by Nathaniel Wilkins, edited by John P. Falcone.*

Game Warehouse, Audio FX Vibrating Headset, Retrieved Feb. 3, 2005. Release date May 3, 2004. http://www.gameswarehouse.com.au/band2.asp?gameid=9780, pp. 1-2.*

CNET Editor's Review of the RCA HP 900 Jun. 11, 2004. Reviewed by Nathaniel Wilkins, edited by John P. Falcome.*

GN Mobile, Jabra BT250v—high performance control, Retrieved Feb. 3, 2005 from Internet Site http://www.jabra.com/JabraCMS/NA/EN/MainMenu/Products/WirelessHeadsets/JabraBT50v/JabraBT250v , pp. 1-2.

Eurotech, HS202 Vibrating Headset, Retrieved Feb. 3, 2005 from Internet Site http://hardware.meetthegeeks.org/ourreview/archives/eurotechhs202, pp. 1-2.

(Continued)

*Primary Examiner* — Devona Faulk

(74) *Attorney, Agent, or Firm* — Ditthavong Mori & Steiner, P.C.

(57) ABSTRACT

A vibrating headset capable of generating a vibration of variable operational characteristics in the earpiece of the vibrating headset is disclosed. The vibrating headset may include one or more earpieces, each of which includes a speaker and a vibrator mechanism, wherein the vibrator mechanism receives a vibration input signal which is distinct from the audio input signal received by the speaker and defines the variable operational characteristics of the vibration to be generated by the vibrator mechanism. A gaming apparatus including a gaming device and a vibrating headset communicably coupled to the gaming device for generating vibrations of variable operational characteristics in response to receiving a vibration input signal from the gaming device is also provided. Finally, a method of creating vibrations defined by at least one variable operational characteristic in an earpiece of a vibrating headset is provided.

24 Claims, 8 Drawing Sheets

OTHER PUBLICATIONS

Jump Shopping, AOpen HP-590 Vibrating Headset, Retrieved Feb. 3, 2005 from Internet Site http://www.jump.co.za/Products/Product.asp?Product__Code=PR000024, pp. 1-2.

Game Warehouse, Audio FX Vibrating Headset, Retrieved Feb. 3, 2005 from Internet Site http://www.gameswarehouse.com.au/longpage.asp?gameid=9780, pp. 1-2.

Game Warehouse, Audio FX, Retrieved Feb. 3, 2005 from Internet Site http://www.gameswarehouse.com.au/band2.asp?s=fullsize&t=rear&g=9780, p. 1.

Lifestyle Fascinations, RCA Vibrating Headphones, Retrieved Feb. 3, 2005 from Internet Site http://www.gadgetbabe.com/showpage.asp?itemid=7790&engine=nxtg& keyword= RC646+ RCA+ vibrating+ headphones++ , p. 1.

* cited by examiner

GAMING HEADSET VIBRATOR

FIELD OF THE INVENTION

The present invention relates generally to an apparatus, and method of using same, that generates vibrations of varying operational characteristics in response to one or more triggers and, more particularly, to a vibrating headset that can be used in conjunction with a gaming device to enhance a gamer's experience.

BACKGROUND OF THE INVENTION

Electronic games have become a widespread entertainment feature that is continuously being modified and improved upon in an effort to enhance a gamer's overall experience. For instance, over time the images of these games have become more life-like, garners have been given the ability to play against other garners in the same room or even in another state, and gaming devices have become so compact that they can be placed in the gamer's pocket and used anywhere. In addition, new gaming accessories have been developed, and existing gaming accessories have been modified, to make game playing even more exciting. One of these accessories is a headset.

Current headsets, some of which may be used in conjunction with industries other than the gaming industry, include speakers that provide audio signals. In conjunction with a game, for example, the audio signals are associated with the current state of the game, such as providing audio signals indicative of crowd noise, the revving of an engine, or the striking of a golf ball. In addition, some of these headsets also provide vibrations that are linked to the audio signals. For example, when a player's car is struck by another car, the headset may provide both a crashing noise and a vibration in order to make the experience more intense. While useful for creating a more realistic gaming experience, these headsets are limited in that the vibrations they generate can only be triggered in conjunction with audio signals being concurrently transmitted to the earpiece of the headset.

BRIEF SUMMARY OF THE INVENTION

Generally described, embodiments of the present invention provide an improvement over the known prior art by providing a vibrating headset capable of generating a vibration of varying operational characteristics in response to receiving a vibration input signal that is distinct from the audio input signal received by the speaker of the vibrating headset. In accordance with embodiments of the present invention, therefore, the vibrating headset is capable of generating varying vibrations independent of whether or not and what type of audio signal may be simultaneously transmitted to the vibrating headset.

In accordance with one aspect of the present invention, a vibrating headset is provided that includes an earpiece having a speaker and a vibrator mechanism, wherein the vibrator mechanism is capable of producing a vibration that is defined by at least one variable operational characteristic. While the speaker receives an audio input signal, the vibrator mechanism of the present invention receives a vibration input signal that is distinct from the audio input signal and defines the variable operational characteristics, such as frequency, amplitude and/or vibration cycle, of the resulting vibration. The vibrator mechanism included in the earpiece may further include a motor and a mass rotatably attached to the motor, such that when the motor is actuated, the mass is rotated by the motor creating the vibration defined by the vibration input signal.

The vibrating headset of the present invention may further include a first and a second conductor for providing the vibration and audio input signals to the vibrator mechanism and speaker, respectively. Alternatively, the vibrating headset may include a single conductor for transmitting both signals. In one embodiment, the vibration and audio input signals are both transmitted over a single conductor using PowerLine Comunications (PLC).

In one embodiment of the present invention, the vibrating headset further comprises a second earpiece also having a speaker and a vibration mechanism. Like the first, the speaker of the second earpiece receives an audio input signal, and the second vibrator mechanism is capable of producing a vibration that is defined by at least one variable operational characteristic, such as frequency, amplitude and/or vibration cycle. These operational characteristics are defined by a second vibration input signal that is distinct from the first vibration input signal and from the audio input signals received by both speakers. In one embodiment of the present invention, the second vibrator mechanism operates independently of the first vibrator mechanism, and vice versa.

In accordance with another aspect of the present invention, a gaming apparatus is provided that includes a gaming device for supporting the operation of at least one electronic game, and a vibrating headset communicably coupled to the gaming device. In one embodiment, the vibrating headset includes an earpiece, which further includes a speaker and a vibrator mechanism, wherein the vibrator mechanism is capable of producing a vibration in response to receiving a vibration input signal from the gaming device. This vibration input signal is distinct from an audio input signal received by the speaker also from the gaming device. According to one aspect of the invention, the vibrator mechanism tailors at least one variable operational characteristic of the resulting vibration based upon the vibration input signal received.

In one embodiment, the gaming device produces the vibration input signal defining the variable operational characteristic of the resulting vibration based upon an activity occurring within the electronic game. The gaming device may further produce the vibration input signal to change the variable operational characteristic of the resulting vibration as the activities occurring within the electronic game change. In one embodiment, the operational characteristics of the resulting vibration that can vary are frequency, amplitude and/or vibration cycle.

In accordance with another aspect of the present invention, a method is provided for creating vibrations defined by at least one variable operational characteristic in an earpiece of a vibrating headset. In one embodiment, the method includes first receiving a vibration input signal defining the variable operational characteristics, and then driving a vibrator mechanism to generate a vibration having the operational characteristics defined by the vibration input signal. The method further includes receiving an audio input signal that is distinct from the vibration input signal, and producing an audio signal in response to the audio input signal. This method may further include, prior to receiving the vibration or audio input signal, multiplexing the audio and vibration input signals over a single conductor.

In one embodiment, the method may further include, prior to receiving the vibration input signal, operating an electronic game on a gaming device, and communicating the vibration input signal based upon an activity occurring within the game. In one embodiment, the method further includes changing the variable operational characteristic defined by the vibration input signal as the activities occurring within the game change.

In one embodiment of the present invention, the step of receiving a vibration input signal further includes receiving a vibration input signal that defines the vibration frequency, and the step of driving a vibrator mechanism to generate a vibration further includes driving the vibrator mechanism to generate a vibration having a vibration frequency defined by the vibration input signal. Alternatively, the step of receiving a vibration input signal may further include receiving a vibration input signal that defines either the vibration amplitude or vibration cycle, and the step of driving a vibrator mechanism to generate a vibration may further include driving the vibrator mechanism to generate a vibration having a vibration amplitude or vibration cycle defined by the vibration input signal.

Other objects, features, and advantages of the present invention will become apparent upon reading the detailed description of the preferred embodiments of the invention below taken in conjunction with the drawings and the appended claims.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

In one embodiment, the vibrating headset of the present invention operates to enhance a gamer's experience by generating vibrations of varying frequency, amplitude and/or vibration cycle within each earpiece of a vibrating headset worn by the gamer while operating an electronic game on his or her gaming device. These vibrations may be triggered by various events taking place within the game, as determined by the game developer. One embodiment of the present invention provides a vibrating headset that includes a vibrator mechanism within each earpiece of the headset. Each vibrator mechanism is driven by a separate, independent vibration input signal generated by the gaming device upon the occurrence of specific events within the game being operated on the gaming device. The vibration input signal determines not only when the vibrator mechanism to which it is transmitted should vibrate, but also at what frequency, amplitude and/or vibration cycle it should vibrate. Having distinct vibration input signals for each vibrator mechanism allows the vibrations in each earpiece of the gamer's headset to be independent of the vibrations in the other, and further to be independent of any audio signal being concurrently transmitted to a speaker also within the earpiece.

Figure 1:
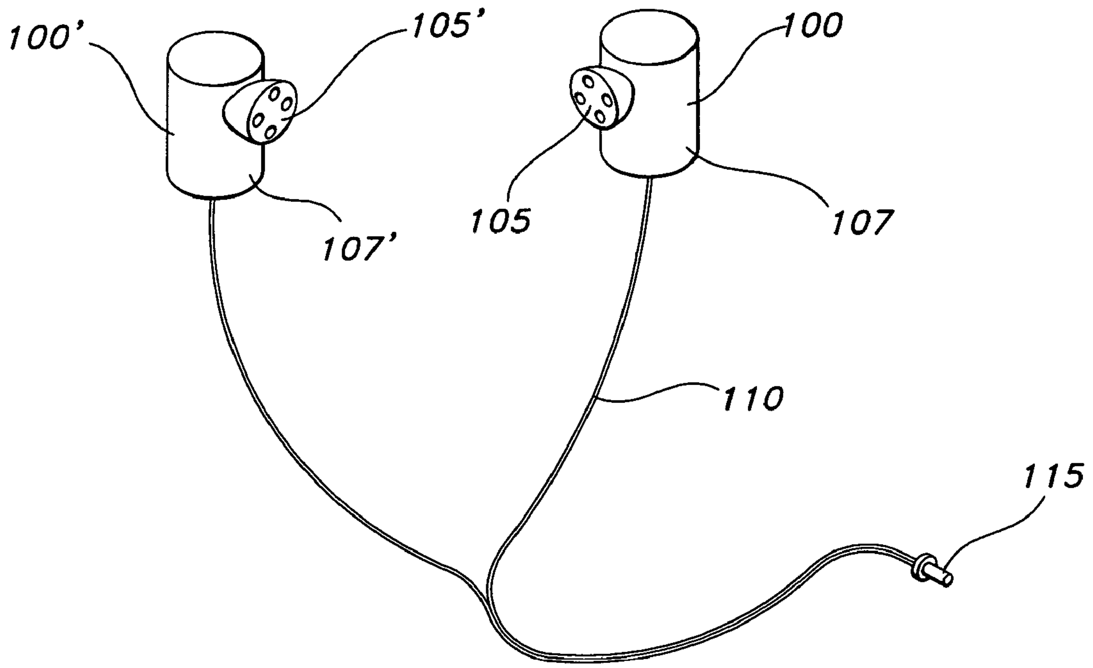
FIG. 1 illustrates a vibrating headset according to one embodiment of the present invention.

FIG. 1 illustrates a vibrating headset according to one embodiment of the present invention. As shown, the vibrating headset includes two earpieces 100, 100', each made up of a shaft 107, 107' and a speaker 105, 105' attached to the outside of the shaft 107, 107'. Other embodiments may include only one earpiece 100, or may include an earpiece 100 that is differently configured, discussed below. According to one embodiment, the vibrating headset further comprises a plug 115 and a cable 110 for removably connecting the vibrating headset to a gaming device and providing a means for transmitting audio and vibration input signals from the gaming device to each earpiece 100, 100'. However, as will be understood by those of ordinary skill in the art, other embodiments of the vibrating headset may operate by transmitting the audio and vibration input signals to each earpiece wirelessly, and thus will not require either a plug 115 or a cable 110.

Figure 2:
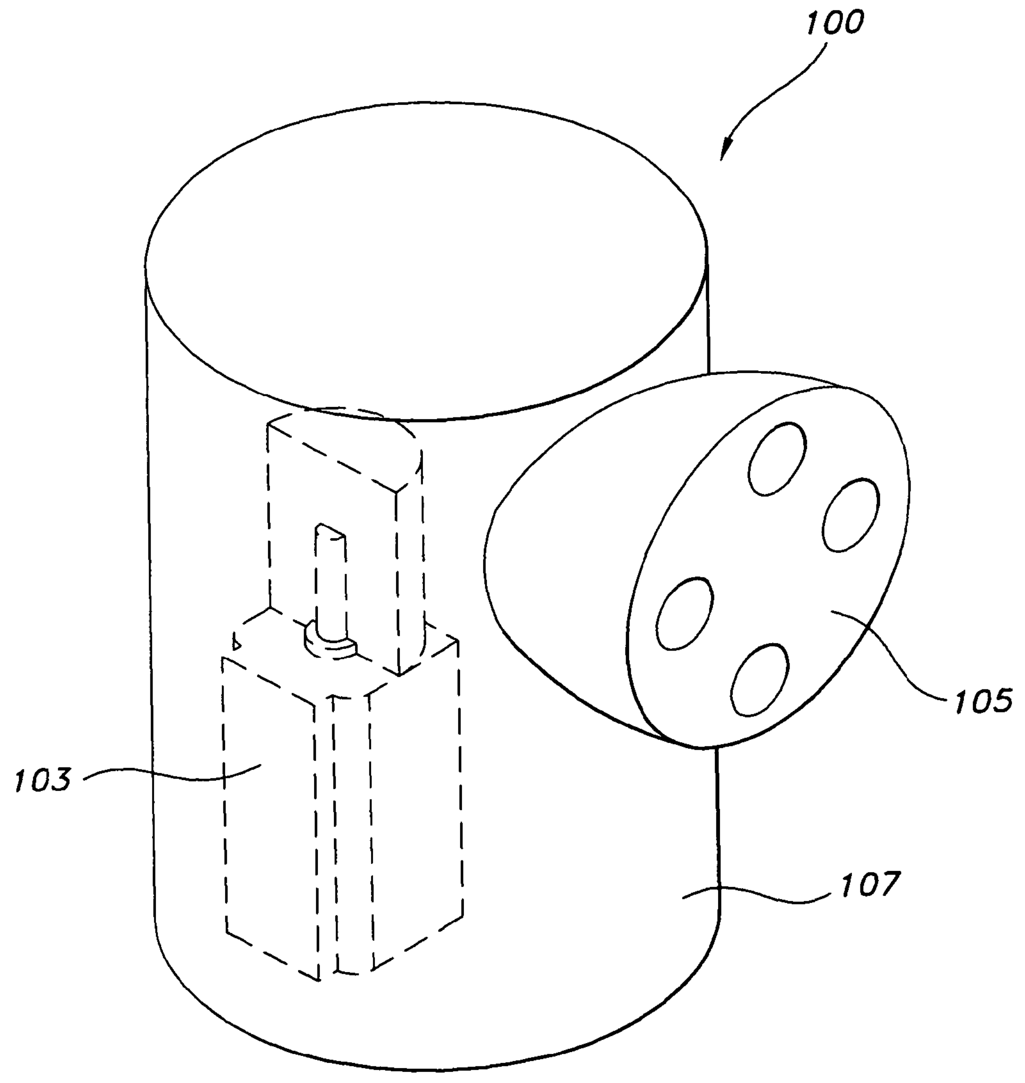
FIG. 2 is a blown-up illustration of an earpiece of a vibrating headset in accordance with an embodiment of the present invention.

In one embodiment, the earpiece 100, shown in more detail in FIG. 2, includes a speaker 105, which forms a hearing-aid style earbud attached to the outside of the earpiece shaft 107. This embodiment enables the speaker 105 to be directly inserted into the gamer's ear. In other embodiments, not shown, the speaker 105 may reside within the earpiece shaft 107. In this embodiment the earpiece 100 would likely rest on the outside of the gamer's ear and be connected to a second earpiece 100' by a headband-type strap that could be placed over the gamer's head. However, the earpiece may be positioned proximate the user's ear in other manners, all of which will be considered headsets in accordance with the present invention.

Figure 3:
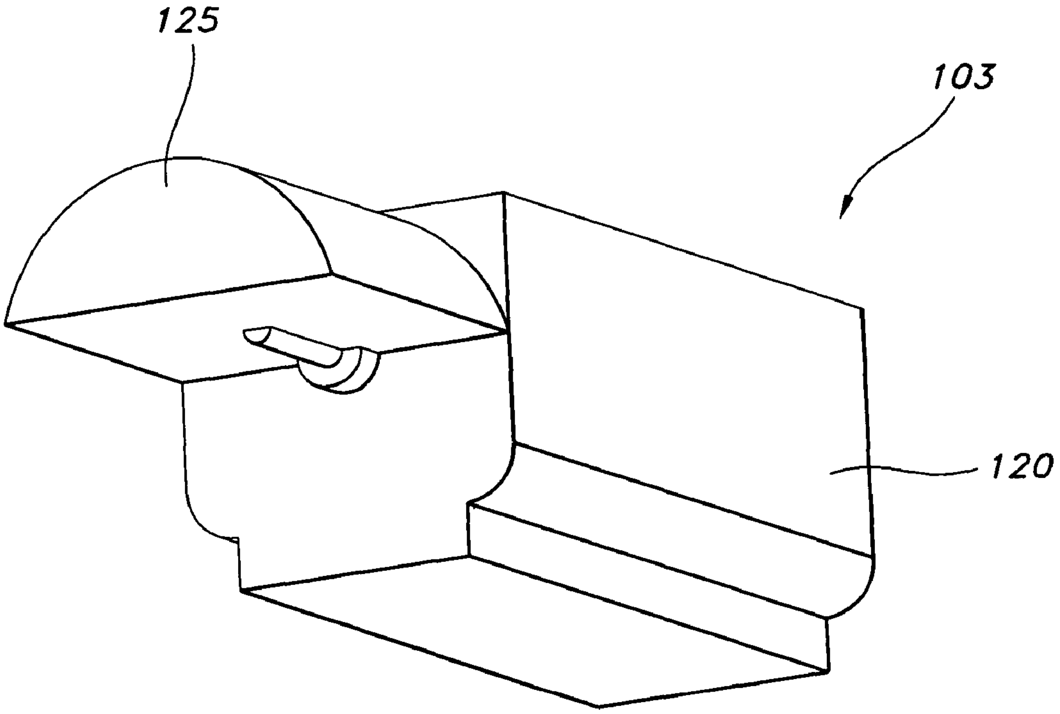
FIG. 3 illustrates a mechanical vibrator for use as the vibrator mechanism within the earpiece of a vibrating headset according to one embodiment of the present invention.

As shown in FIG. 2, the earpiece shaft 107 of one embodiment of the present invention is at least partially hollow, enabling a vibrator mechanism 103 to be housed within the shaft 107. In one embodiment, the vibrator mechanism 103 is a mechanical vibrator, shown in detail in FIG. 3. However, other embodiments of the present invention may use an acoustic or other type of vibrator mechanism to generate the various vibrations in each earpiece. As will be understood by those of skill in the art, a mechanical vibrator comprises a motor 120 with an offset mass 125 rotatably attached to the motor 120. As the motor 120 is actuated, the offset mass 125 is rotated to create a vibration, the frequency of which is determined by the speed of the motor 120. The operational characteristics of the resulting vibration, such as frequency, and/or vibration cycle, can therefore be manipulated by turning the motor on and off in various intervals and by rotating the offset mass 125 while the motor 120 is turned on at various speeds.

In one embodiment of the present invention, a DC (Direct Current) motor may be used in the mechanical vibrator. As will be understood by those of ordinary skill in the art, the speed of a DC motor varies as the voltage of the power signal that is driving the motor is varied. In other words, when a vibrator mechanism 103 comprising a DC motor-driven mechanical vibrator is used to generate vibrations in the earpiece 100 of a vibrating headset, vibrations of varying frequencies can be generated by varying the voltage of the power signal transmitted to the vibrator mechanism 103 by the gaming device. This may be done by using a voltage controller within the gaming device itself. In one embodiment, the DC motor may operate by processing a square wave that is alternating between 0 and 3V. The voltage of this square wave can then be fluctuated between 0 and 3V in order to vary the speed of the motor, and therefore the frequency of the vibration.

Figure 4A:
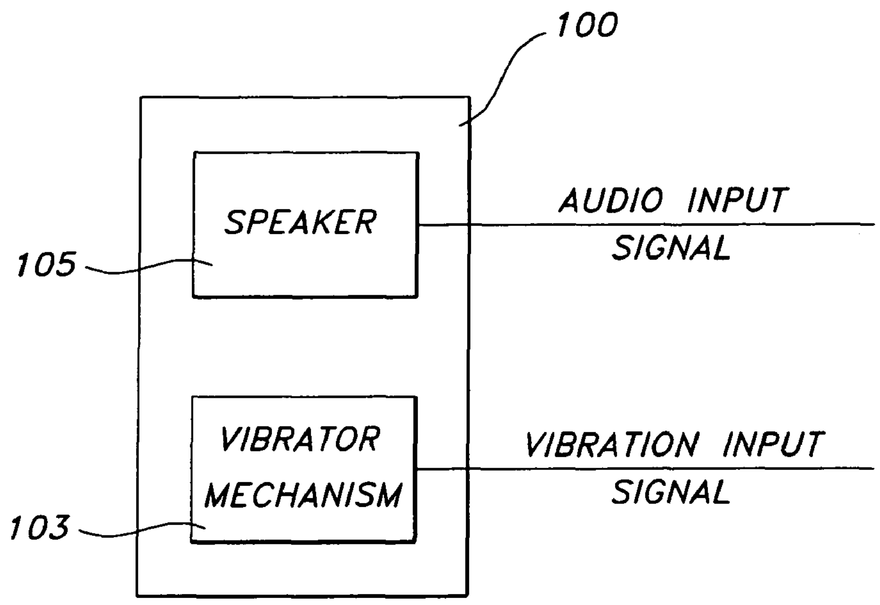
FIGS. 4A is a block diagram of an earpiece of a vibrating headset according to one embodiment of the present invention.
Figure 4B:
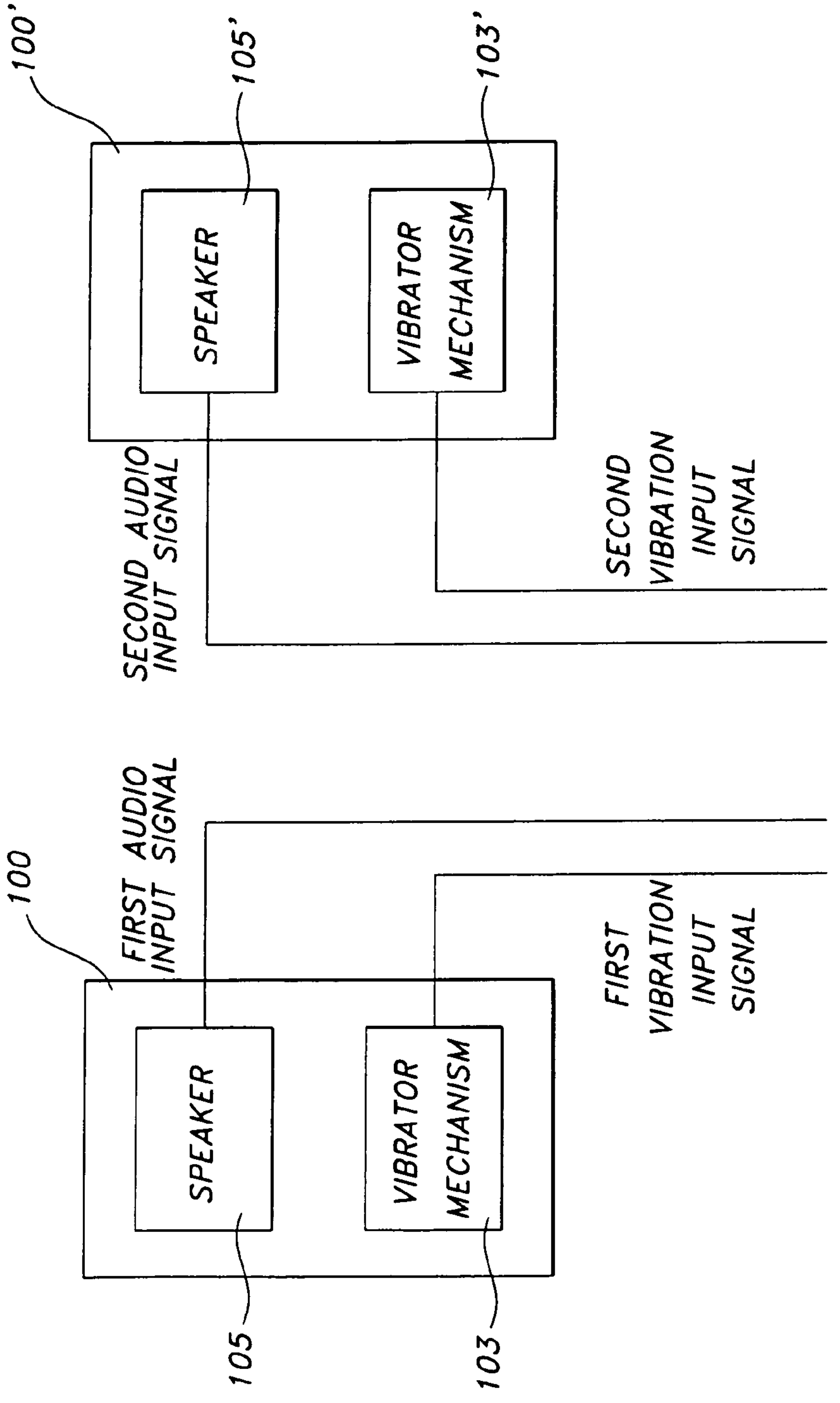
FIG. 4B is a block diagram of a pair of earpieces of a vibrating headset according to one embodiment of the present invention.

As discussed above, according to one embodiment of the present invention, vibrations of varying frequency, amplitude and/or vibration cycle can be generated within each earpiece of a vibrating headset by manipulating a vibration input signal being transmitted to the earpiece by a gaming device to which the vibrating headset is connected. In one embodiment, this vibration input signal is distinct for each earpiece, and is further distinct from any audio input signal being concurrently transmitted by the gaming device to the speaker of the earpiece. This is illustrated in FIGS. 4A and 4B. As shown in FIG. 4A, two distinct and independent signals, a vibration input signal and an audio input signal, are separately transmitted to the vibrator mechanism 103 and speaker 105, respectively. By having distinct vibration and audio input signals, vibrations of varying operational characteristics can be generated within the earpiece 100 of the vibrating headset independent of any audio input signals being transmitted to the speaker 105 of the vibrating headset. In other words, when a gamer is using his or her vibrating headset while operating an electronic game on his or her gaming device, he or she will be able to feel a vibration in his or her ear(s) of varying frequency, amplitude, and/or vibration cycle upon the occurrence of particular events within the game, regardless of what, if any, sound he or she is hearing. For example, in the instance where the electronic game being operated involves underwater combat, while no sound would he heard when there is an explosion near the gamer's player, in order to enable the gamer to "feel" the explosion, a vibration could be generated in either or both earpieces of the vibrating headset. Generating these vibrations enables the gamer to more fully experience the game he or she is playing, and in turn makes it more exciting.

FIG. 4B illustrates an embodiment where there are two earpieces 100, 100', each comprising a speaker 105, 105' and a vibrator mechanism 103, 103'. As shown, two vibration input signals, a first and a second, are independently transmitted to each vibrator mechanism 103, 103', while two audio input signals, a first and a second, are separately transmitted to each speaker 105, 105'. In this embodiment, the separate vibration input signals enable a gamer to experience separate vibrations of varying frequency, amplitude and/or vibration cycle in each ear. For example, the electronic game could be written such that when contact is made with the gamer's character from the left or right side, his or her corresponding earpiece alone would vibrate. Alternatively, the gamer could receive a vibration in both ears when, for example, his or her player is blown up.

In one embodiment of the present invention, wherein the vibrating headset comprises two earpieces, four separate conductors are used to transmit the separate signals—i.e., the first and second vibration input signals, and the first and second audio input signals. In this embodiment, standard audio cables can be used to deliver the high frequency audio signals to each of the speakers 105, 105', while two separate power cables are required to transmit the first and second vibration input signals. In another embodiment, no separate audio cables are required. In this embodiment, each high frequency audio signal is transmitted over a corresponding power line carrying the first or second vibration input signal. In one embodiment, this is done using PowerLine Communications (PLC) (http://www.powerlineworld.com/oowerlineintro.html), which utilizes power lines for the high-speed transmission of data and voice services. Using PLC, high frequency audio signals and low frequency power signals can be transmitted together over the same conductor without affecting each other. In yet another embodiment, the audio and vibration input signals may be transmitted wirelessly to the speaker and vibration mechanism, respectively.

As discussed above, vibrations of varying frequency, amplitude and/or vibration cycle can be generated in each earpiece of a vibrating headset according to embodiments of the present invention. In one embodiment, these vibrations are triggered by specific events occurring in an electronic game operating on a gaming device to which the vibrating headset is connected. These occurrences dictate not only when the vibration occurs, but also at what frequency, amplitude and/or vibration cycle.

Figure 5:
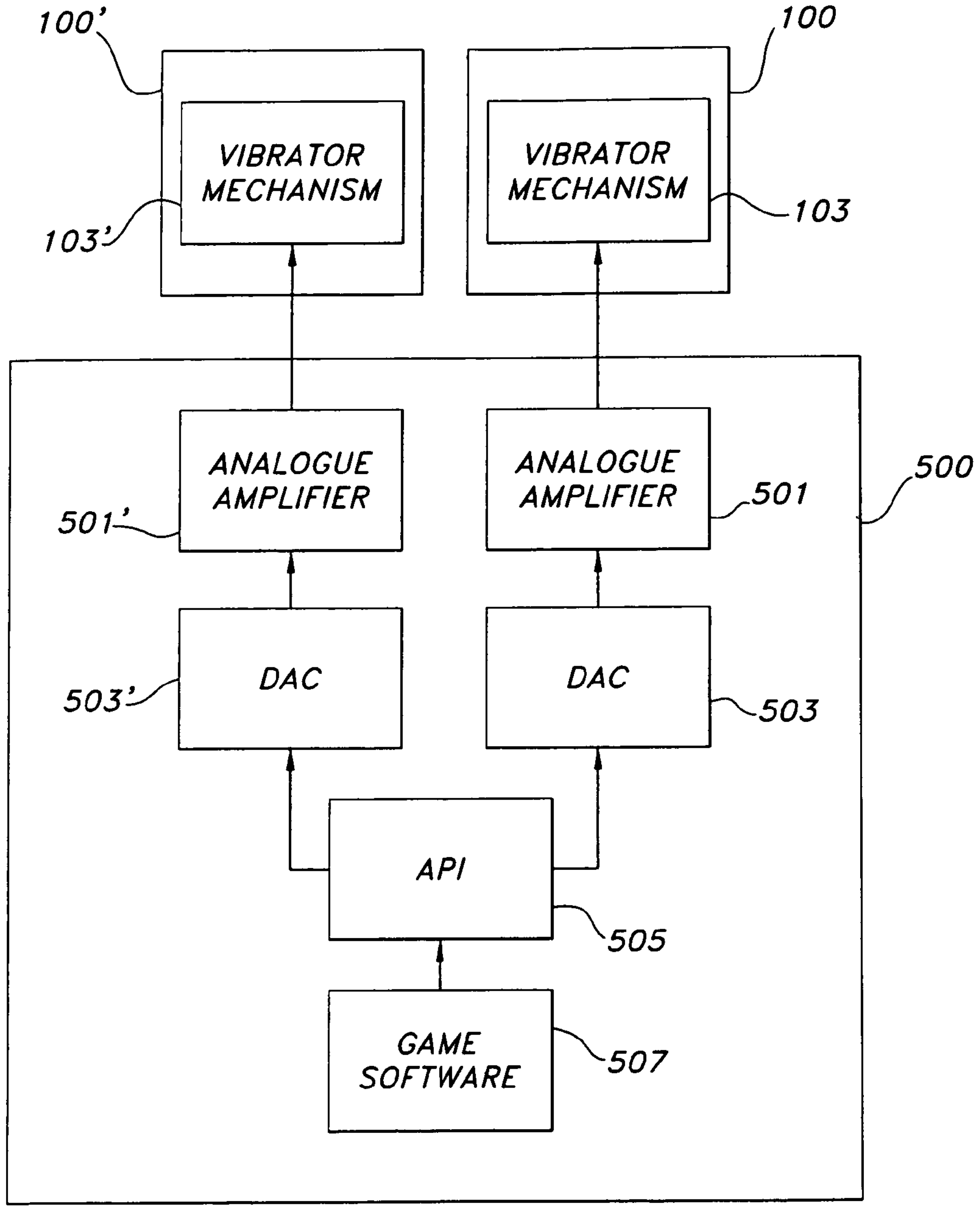
FIG. 5 is a block diagram of a gaming device and headset according to one embodiment of the present invention.

In one embodiment, in developing their games, game developers can use an application program interface (API) that defines a set of routines for directing vibrations of various characteristics, e.g., frequency, amplitude and/or vibration cycle, within the vibrating headset. As illustrated in FIG. 5, when a routine within the API 505 is called by the game software 507 developed by the game developer, the API 505 transmits a software signal corresponding with the vibration to be generated (i.e., indicating the frequency, amplitude and/or vibration cycle of the resulting vibration) to a Digital to Analogue Converter (DAC) 503, 503', corresponding with the vibrator mechanism 103, 103' to be vibrated, where the digital software signal is converted into an analogue signal. The resulting analogue signal can then be transmitted to an analogue amplifier 501, 501', which in turn will power the corresponding vibrator mechanism 103, 103'. As shown, each vibrator mechanism 103, 103' is powered by a separate analogue amplifier 501, 501', which itself receives a separate analogue signal from a corresponding DAC 503, 503'. In addition, in one embodiment, the game software 507, API 505, DACs 503, 503', and analogue amplifiers 501, 501' each reside, at least temporarily, on the gaming device 500 itself.

As an example, in one embodiment of the present invention, where no vibration is triggered, the signal transmitted by the API 505 is a series of zeroes. By contrast, when a vibration is triggered, the API 505 will send a series of 1s, 2s, 3s, 4s, etc., depending on the frequency of the vibration to be triggered, to the DAC 503, 503' associated with the vibrator mechanism 103, 103' to be vibrated. The signal transmitted by the API 505 may further be varied by incorporating a series comprising 0s, 1s, 2s, 3s, 4s, etc. in varying combinations, thus triggering a vibration of varying vibration cycle.

When developing his or her game, the game developer defines the parameters for each routine in each game he or she develops. For instance, the API may specify that vibration of type X (e.g., left vibrator mechanism only, x frequency, vibration cycle=constant for y seconds) is generated by routine Y. The game developer can then define the parameters of that routine within the software code for each game. For example, the game developer may specify in the software of game A that when a player is punched in the left side of his or her body, routine Y should be called, while specifying in the software of game B that routine Y should be called with the player's car is struck from the left side.

As an example, in a game such as a First Person Shooter Game the game developer may decide that anything affecting the "health" points of the player should trigger a vibration. He or she may further decide that the intensity of the vibration should vary based upon the magnitude of the injury, while the location of the injury should determine whether the left, right or both earpieces will generate the vibration. The game developer would then define the parameters of each routine in the API that he or she wishes to call to conform to these specifications. For example, the game developer may define the parameters of a particular routine so that if an injury is received on the player's left side, the vibrator mechanism in the left earpiece of the vibrating headset is activated, and if the injury is on the player's right side, the right vibrator mechanism is activated. Conversely, if the player is attacked from the front or back, the game developer may have the software call the vibration routine that activates both vibrator mechanisms. Other triggers the game developer may use might include falling from a high building, running through hot flames or drowning under water. Another example may relate to Car Racing Games. For this type of game, the game developer may likewise decide that any action that damages the car should cause at least one of the vibrator mechanisms within the vibrating headset to be triggered. Again, he or she may define the parameters of various vibration routines called by the game software so that the location of the damage dictates which of the left, right or both earpieces vibrate, and the magnitude of the damage dictates the intensity of each vibration.

Figure 6A:
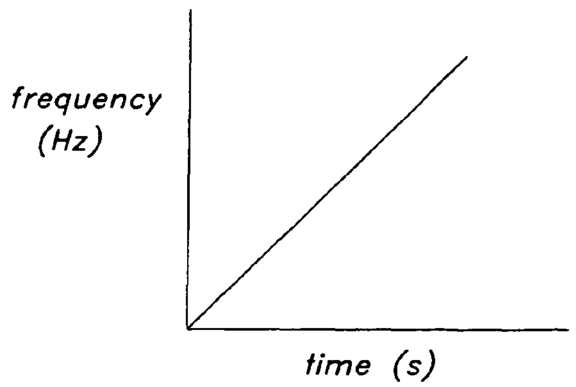
FIGS. 6A, 6B and 6C illustrate various vibration cycles that could be generated by a vibrator mechanism of a vibrating headset in response to one of a plurality of triggers according to one embodiment of the present invention.
Figure 6B:
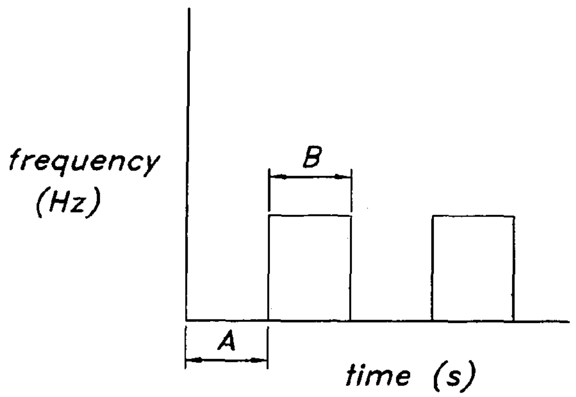
Figure 6C:
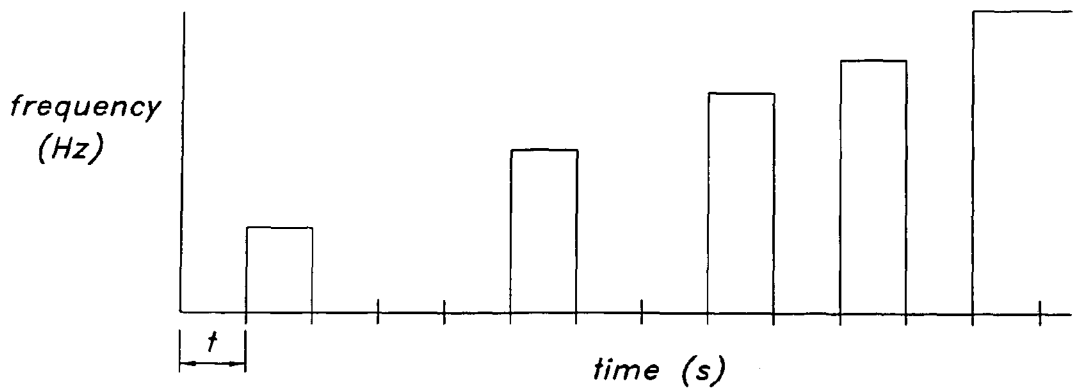

FIGS. 6A, 6B and 6C illustrate one way to modify the vibration based on a particular event occurring within the game through the use of various vibration cycles. According to embodiments of the present invention, a vibration cycle is defined by the amount of time, at what intervals, and at what frequency each vibration is generated. As an illustration, imagine that the gamer is playing a game in which he or she is being chased by his or her opponent. In such a game, while the gamer may not be able to see or hear when the opponent is approaching from behind, it would make the experience more exciting if he or she were able to feel the opponent getting closer. To simulate this feeling, various vibration cycles could be used. FIG. 6A illustrates a first vibration cycle in which the frequency, and therefore the intensity, of the vibration steadily increases over time as the opponent gets closer. In FIG. 6B, the footsteps of an opponent can be simulated by causing the vibrations to turn on and off at various intervals. As shown, in one example, the vibration may be off for A seconds, on for B seconds, off for A seconds, and so on and so forth. These increments could remain constant throughout the vibration cycle, or they could be varied by, for example, steadily decreasing A and increasing B in an effort to create the impression that the opponent is getting closer. The vibration cycle could be further modified, as shown in FIG. 6C, by not only steadily decreasing the amount of time the vibration is off and increasing the amount of time it is on, but by also steadily increasing the frequency of the vibration as time passes.

Figure 7:
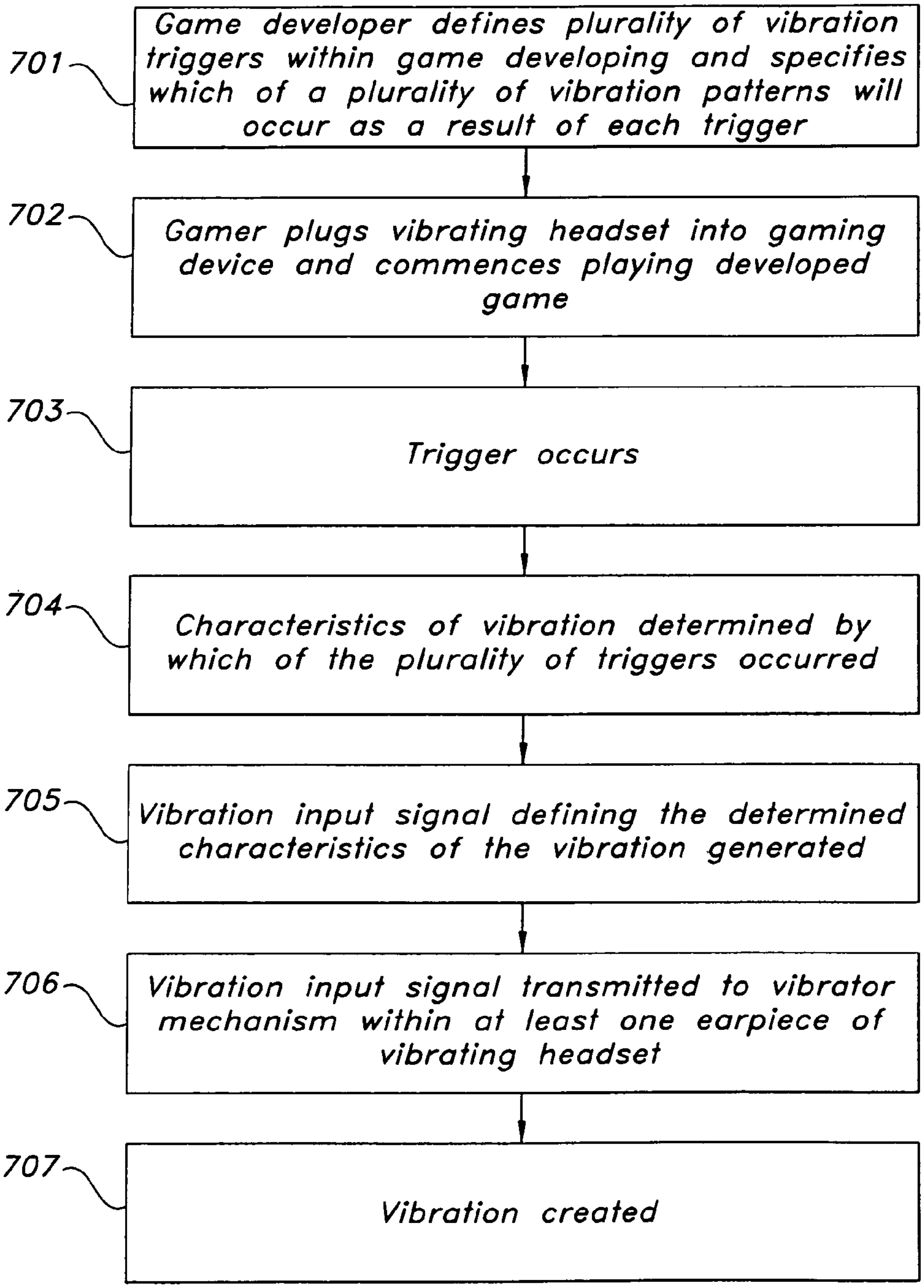
FIG. 7 is a flow chart for a method of creating a vibration in a vibrating headset according to one embodiment of the present invention.

FIG. 7 is a flow chart illustrating a method of creating a vibration in the vibrating headset according to one embodiment of the present invention. In Step 701, a game developer defines a plurality of vibration triggers within the game that he or she is developing and specifies which of a plurality of vibration patterns will occur as a result of each trigger. To do this, as discussed above, in one embodiment of the present invention, the game developer adds software to his or her game that will cause various vibration routines to be called from an API in response to various defined parameters being met, such as a player being struck from the left. These vibration routines define the operational characteristics of each vibration associated with each trigger.

In Step 702, a gamer plugs his or her vibrating headset into a gaming device and commences playing the game developed in Step 701. While playing, in Step 703, one of the plurality of triggers defined by the game developer occurs—e.g., the player is shot in his or her right arm. In Step 704, the characteristics of the vibration associated with that trigger are determined by reference to the called routine in the API. In response, in Step 705 a vibration input signal to generate a vibration of those characteristics is created within the gaming device. As discussed above, in one embodiment, this vibration input signal can be created by transmitting a software signal generated by the API, which defines the characteristics of the vibration to be triggered, to a DAC where it is converted into an analogue signal and further transmitted to an analogue amplifier, which in turn will power the corresponding vibrator mechanism. As stated above, the digital signal transmitted by the API may, in one embodiment, consist of a serious of alternating 0s, 1s, 2s, 3s, 4s, etc. in varying intervals in order to generate a vibration of varying frequency and/or vibration cycle.

In Step 706, the resulting vibration input signal is transmitted to at least one vibrator mechanism within the vibrating headset comprising a motor and an offset mass. Finally, in Step 607, the motor of the vibrator mechanism receiving the vibration input signal is actuated in the intervals and at the speeds specified by the vibration input signal creating a vibration of the operational characteristics specified by the called routine corresponding to the particular trigger which occurred.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus comprising:

an earpiece, wherein said earpiece comprises:

- a speaker configured to be inserted into an ear and receptive to an audio input signal; and
- a vibrator configured to produce a vibration defined by at least one variable operational characteristic, wherein said vibrator is receptive to a vibration input signal that is independently defined from said audio input signal and defines the variable operational characteristic of the resulting vibration.

2. The apparatus of claim 1, wherein said vibrator is configured to produce a vibration defined by at least one of a variable frequency, a variable amplitude, and a variable vibration cycle.

3. The apparatus of claim 1, wherein said vibrator comprises:

a motor; and a mass rotatably attached to said motor such that said mass rotates upon actuation of said motor to create the vibration.

4. The apparatus of claim 1 further comprising first and second conductors configured for providing the vibration input signal and the audio input signal to said vibrator and said speaker, respectively.

5. The apparatus of claim 1, further comprising a single conductor configured for providing both the audio input signal and the vibration input signal in a multiplexed fashion.

6. The apparatus of claim 5, wherein the audio input signal and the vibration input signal are provided over said single conductor using PowerLine Communications (PLC).

7. The apparatus of claim 1 further comprising:

a second earpiece connected to said first earpiece, wherein said second earpiece is further comprised of:

a second speaker receptive to a second audio input signal; and a second vibrator configured to produce a vibration defined by at least one variable operational characteristic, wherein said second vibrator is receptive to a second vibration input signal that is distinct from said second audio input signal and defines the variable operational characteristic of the resulting vibration.

8. The apparatus of claim 7, wherein the first and second vibrators operate independently of each other.

9. A method comprising:

receiving a vibration input signal defining at least one variable operational characteristic, the vibration input signal being independently defined from an audio input signal;

determining to drive a vibrator to generate a vibration having the at least one variable operational characteristic defined by the vibration input signal;

receiving the audio input signal via a speaker that is configured to be inserted into an ear, the audio input signal is distinct from said vibration input signal; and producing an audio sound in response to said audio input signal.

10. The method of claim 9, wherein prior to receiving the vibration input signal, said method further comprises:

determining to operate an electronic game on a gaming device to which said vibrating headset is connected; and determining to communicate said vibration input signal upon one or more activities occurring within said electronic game.

11. The method of claim 10 further comprising:

determining to electronically change the at least one variable operational characteristic defined by said vibration input signal as the one or more activities occurring within the electronic game change.

12. The method of claim 9, wherein the vibration input signal defines at least one of a vibration frequency, a vibration amplitude, and a the vibration cycle, and wherein the vibrator is driven to generate a vibration having the at least one of the vibration frequency, the vibration amplitude, and the vibration cycle defined by said vibration input signal.

13. The method of claim 9, wherein prior to receiving a vibration input signal and receiving an audio input signal, said method comprises:

determining to multiplex said audio input signal with said vibration input signal over a single conductor.

14. The method of claim 13, wherein the single conductor provides said audio input signal and said vibration input signal, respectively, using PowerLine Communications (PLC).

15. The method of claim 9, wherein said vibrator comprises:

a motor; and a mass rotatably attached to said motor such that said mass rotates upon actuation of said motor to create the vibration.

16. An apparatus comprising:

a first earpiece, wherein said first earpiece comprises:

a first speaker receptive to an audio input signal; and a first vibrator configured to produce a first vibration defined by a first at least one variable operational characteristic, wherein said first vibrator is receptive to a first vibration input signal that is distinct from said audio input signal and defines the first at least one variable operational characteristic of the resulting first vibration;

a second earpiece connected to said first earpiece, wherein said second earpiece comprises:

a second speaker receptive to the audio input signal; and a second vibrator configured to produce a second vibration defined by a second at least one variable operational characteristic, wherein said second vibrator is receptive to a second vibration input signal that is distinct from said audio input signal and defines the second at least one variable operational characteristic of the resulting second vibration; and wherein the first and second vibrators operate independently of each other.

17. The apparatus of claim 16, wherein each of said first and second vibrators are configured to produce a vibration defined by at least one of a variable frequency, a variable amplitude, and a variable vibration cycle.

18. The apparatus of claim 16, wherein each of said first and second vibrators comprise:

a motor; and a mass rotatably attached to said motor such that said mass rotates upon actuation of said motor to create the vibration.

19. The apparatus of claim 18 further comprising first and second conductors configured to provide the first and second vibration input signals and the audio input signal to said first and second vibrators and said first and second speakers, respectively.

20. The apparatus of claim 18, further comprising a single conductor configured to provide both the audio input signal and the first and second vibration input signals in a multiplexed fashion.

21. The apparatus of claim 20, wherein the audio input signal and the first and second vibration input signals are provided over said single conductor using PowerLine Communications (PLC).

22. An apparatus comprising:

at least one processor; and at least one memory including computer program code, the at least one memory and the computer program code configured to, with the at least one processor, cause the apparatus to perform at least the following, receive a vibration input signal defining at least one variable operational characteristic, the vibration input signal being independently defined from an audio input signal;

determining to drive a vibrator to generate a vibration having the at least one variable operational characteristic defined by the vibration input signal;

receive the audio input signal via a speaker that is configured to be inserted into an ear, the audio input signal is distinct from said vibration input signal; and determine to produce an audio sound in response to said audio input signal.

23. The apparatus of claim 22, wherein the at least one variable operational characteristic includes at least one of a variable frequency, a variable amplitude, and a variable vibration cycle.

24. The apparatus of claim 22, wherein the apparatus receives the audio input signal and the vibration input signals in a multiplexed fashion.

* * * * *